United States Patent
Reda et al.

(10) Patent No.: US 9,862,996 B2
(45) Date of Patent: *Jan. 9, 2018

(54) BIOSENSOR ARRAY FORMED BY JUNCTIONS OF FUNCTIONALIZED ELECTRODES

(75) Inventors: Torsten Reda, Vienna (AT); Jakob Haglmueller, Vienna (AT); Georg Schitter, Vienna (AT); Alexander Seitz, Vienna (AT)

(73) Assignee: Lexogen GmbH, Vienna (AT)

( * ) Notice: Subject to any disclaimer, the term of this patent is extended or adjusted under 35 U.S.C. 154(b) by 924 days.

This patent is subject to a terminal disclaimer.

(21) Appl. No.: 14/001,927

(22) PCT Filed: Feb. 27, 2012

(86) PCT No.: PCT/AT2012/000042
§ 371 (c)(1),
(2), (4) Date: Aug. 28, 2013

(87) PCT Pub. No.: WO2012/116385
PCT Pub. Date: Sep. 7, 2012

(65) Prior Publication Data
US 2013/0331299 A1    Dec. 12, 2013

(30) Foreign Application Priority Data
Feb. 28, 2011   (EP) .................................... 11450028

(51) Int. Cl.
C12Q 1/00      (2006.01)
C12Q 1/68      (2006.01)
G01N 27/327    (2006.01)

(52) U.S. Cl.
CPC ......... *C12Q 1/686* (2013.01); *G01N 27/3278* (2013.01); *C12Q 1/6837* (2013.01)

(58) Field of Classification Search
CPC ............. G01N 27/327; G01N 27/3271; G01N 27/3275; G01N 27/3278; G01N 33/5438; G01N 33/553; B82Y 15/00; C12C 1/6825
USPC .................. 204/400, 403.01, 403.02, 403.03
See application file for complete search history.

(56) References Cited

U.S. PATENT DOCUMENTS

2009/0188784 A1   7/2009  Lee et al.
2012/0122715 A1*  5/2012  Gao ................... G01N 27/3278
                                                            506/9

FOREIGN PATENT DOCUMENTS

EP   2088430 A1      8/2009
WO   2010104479 A1   9/2010

* cited by examiner

*Primary Examiner* — Dwayne K Handy
(74) *Attorney, Agent, or Firm* — Laurence A. Greenberg; Werner H. Stemer; Ralph E. Locher

(57) ABSTRACT

The present invention provides a sensor array device with multiple sensor junctions which have been created through the assembly of two or more differently functionalized surfaces. The functionalizing of the prospective sensor junction areas with sensor compounds occurred when the different surfaces were physically separated from each other before the assembly of the sensor array. By these means, sensor junctions can be built smaller than conventional deposition techniques like printing and photolithography would allow for otherwise. As a consequence, each individual sensor junction contains two potentially different sensor compounds. The sensor array identifies and quantifies different biomolecules.

15 Claims, 7 Drawing Sheets

| Spotted Primer | | | | | | | Signal $F_{532} - B_{532}$ |
|---|---|---|---|---|---|---|---|
| Forward   | • | • | • | • | • | • | 8.823 |
| Reverse   | · | · | · | · | · | · | 697 |
| Mix       | · | · | · | · | · | · | 4.105 |
| Guide Dot | • | • | • | • | • | • | saturated |
| Forward   | • | • | • | • | • | • | 8.772 |

Fig. 13

BIOSENSOR ARRAY FORMED BY JUNCTIONS OF FUNCTIONALIZED ELECTRODES

The present invention provides a sensor array device with multiple sensor junctions which have been created through the assembly of two or more differently functionalized surfaces. The functionalizing of the prospective sensor junction areas with sensor compounds occurred when the different surfaces were physically separated from each other before the assembly of the sensor array. By these means, sensor junctions can be built smaller than by using conventional deposition techniques like printing and photolithography would allow for otherwise. As a consequence, each individual sensor junction contains two potentially different sensor compounds. The sensor array identifies and quantifies different biomolecules.

FIELD OF INVENTION

The present disclosure relates to the detection of biomolecules via dedicated sensor array devices. More specifically, the present disclosure addresses the multiplexed, parallel detection of linear biopolymers such as DNA, RNA or proteins, also addressed as analyte, and we present for this purpose a device for the dual detection of biopolymers that employs two modified surfaces for analyte characterization within formed nanogaps. Parallel detection of two distinct features of biomolecules enhances the accuracy in identification of biomolecules. Furthermore, the present disclosure relates to linear and exponential amplification of biomolecules and subsequent signal enhancements methods within confined gap areas.

Sensor devices have found numerous applications with the aim of gaining knowledge on the constituents of complex mixtures of biomolecules. One class of biomolecules, nucleic acids, has received particular attention due to their fundamental biological importance. As consequence, the different kinds and concentrations of DNA and RNA are of great interest for scientific, clinical and forensic uses.

Living cells contain genomic DNA, a quasi-static set of few extremely large molecules, the chromosomes. Cells also harbor another class of nucleic acids, the RNA. The sum of all RNA molecules is denoted as the transcriptome, the sum of all transcripts. In contrast to the genomes transcriptomes are highly complex and dynamic mixtures of all present gene products. The sequences of different transcripts of the same gene can vary in their start and/or end site as well as in parts of their internal sequence and are called transcript or splice variants. The abundances of transcripts define the dynamic state of cells. Transcripts execute the genomic information content.

Proteins are the translational products of transcripts and mirror to large parts the transcriptomic information but are subject to post-translational modifications which introduce another dimension of complexity to the proteome, the entirety of all proteins.

Characterizations of mixtures of different analytes can be performed though parallel measurements with dedicated sensor arrays.

The principal task of the present invention is to describe a functional design of sensor arrays for the analysis of complex mixtures of biomolecules. Such sensor arrays have to be highly suitable for quasi-simultaneous processing of numerous measurements of small precious sample sizes which implies miniaturization and automation.

BACKGROUND OF THE INVENTION

Current technologies for polynucleic acid analysis are diverse and include PCR (polymerase chain reaction) and quantitative PCR, RNA- or cDNA-microarrays, 3'- and 5' RACE, rapid amplification of cDNA ends, cap analysis of gene expression, CAGE, serial analysis of gene expression, SAGE, cloning experiments, Sanger sequencing, massively parallel sequencing also known as next generation sequencing, NGS and SQUARE, a primer matrix based segregation method which groups the transcriptome into classes of molecules which share the same start- and end sequences [Seitz, 2007]. The field of protein analysis methods is much wider. Complex proteomes are studied by 2D and 3D electrophoresis, which separate proteins due to their physical properties, mass spectrometry for the high-throughput identification of proteins and sequencing of peptides, protein microarrays to detect relative protein concentrations, or two-hybrid screening for the exploration of protein-protein and nucleic acid-protein interactions.

NGS technologies are tag-based methods to sequence genomes and transcriptomes. One example is its combination with RNA-Seq which extracts random short sequence fragments from RNA molecules. Despite obvious advantages like hypothesis neutrality, which means that this method can be applied without pre-knowledge, several drawbacks are evident. First, NGS systems and kits are costly in terms of manpower, time, material consumption and data processing power. Second, detection of low gene expression levels is only possible if samples are sequenced to extreme depth, which means in turn that common transcripts are read manifold before rare reads become visible. Third, the detection of transcript isoforms remains probabilistic and heavily relies on a-priori information. Independent of the applied read depth many reads cannot be uniquely assigned to the correct transcript as soon as alternatives are possible. The transcript pattern remains diffuse and often gene expression patterns, which group all gene related transcripts, are presented instead of transcriptome patterns. It contributes to the reduced applicability of NGS methods in the analysis of highly complex samples.

One hurdle lies in the entropy of systems as a measure of disorder or randomness of its constituents. Characterizing disordered systems requires identifying all individual constituents and assigning them to one group of equals, e.g. to the correct transcript. Methods which segregate the constituents in complex systems reduce their entropy. This implies that after segregation information can be gained easier because then it only requires identifying the group and the number of constituents per group. Such methods are described below on the example of transcriptome analysis For microarray experiments different oligonucleotide probes are immobilized in separate spots on a supporting solid surface. By these means, microarrays allow to separate samples into different classes of molecules due to the hybridization of analytes to those probes. One major drawback is their lack of discriminatory power to distinguish cognate sequences, e.g. splice variants. Molecules which carry the same sequence anywhere in the molecule equally hybridize to the same probes. Cross-hybridizations are common and blur the results.

The use of two probes, and in particular two probes which have been designed as primers for PCR amplification reactions, helps to alleviate the problems of such cross-hybridization. PCR measures the presence of individual sequences. Measurements of a moderate number of different analytes in a mixture can be achieved in parallel fluid phase formats for example using multi-well PCR plates. However, the number of targeted analytes is much too small to investigate complex transcriptomes in depth.

Bridge PCR combines the multiplexing capabilities of microarrays with the accuracy and sensitivity of PCR-based assays. Here, the immobilization of primer pairs enables solid phase supported reactions. The two primers are immobilized to a single sensor surface either as a mixture or sequentially to form a mixed layer of primers at the surface which becomes very challenging for larger arrays. If a target molecule binds to such a surface it can initiate a seed for amplification and in succession a surface mediated PCR reaction. One difficulty results from the fact that different sites of the analyte molecule reacts with the very same surface. This means, the analyte and its copies should not stick to the surface to enable the efficient enzyme catalyzed polymerization, but "bends" towards this surface in order to react with the second probe. This structure sparked the name "bridge amplification". The bridges spread across the same surface. Initial seed islands grow geometrically which means that the further extension occurs predominantly along their edges and the effective amplification efficiency decreases progressively [Mercier, 2003; Adessi, 2000].

Beside optical detection of molecular recognition events which are predominantly based on corresponding labeling methods alternative approaches exist which are exploiting the electrical properties of biomolecules. Capacitive biosensors were disclosed in U.S. Pat. No. 5,532,128, US 20040110277 or WO 2009003208. Herein, the general principle uses changes in the dielectric properties which lead to a change of the capacitance of sensor elements. Measurements between closely spaced electrodes or conductors which form tiny nanometer sized gaps promise sensitivities high enough to detect very few molecules and even single molecules. The production of said gaps is technologically difficult but feasible. Techniques like electron beam lithography [Hwang, 2002], electrodeposition and -migration [Iqbal, 2005], composite layer build-up and etching [WO 2009003208] and different fracture techniques [Reed, 1997; Reichert, 2002] have been applied to separate two conductors by such nanometer sized gaps.

For the detection of molecules which have more than one recognition site it is advantageous to modify each of two opposite conductors with a different molecular probe. But, such kind of individual conductor modification is challenging when it comes to nanometer dimensions. In WO 2009003208 Steinmuller-Nethl et al. have proposed to use different materials for each conductor while the conductors are separated trough an insulating layer with a thickness of only several nanometers. The different conductor materials enable the successive and selective binding of the molecular probes. As the number of electrically conducting but different materials in line with a specific and effective binding chemistry is limited, such an approach is not applicable for building large arrays.

Gao and Chen [WO 2010104479 A1] made electrode-insulator-electrode sandwich assemblies with stepped arrangements of electrodes which are separated by few nanometers thick layer of for example silicon oxide. Here, the electrode array structures were made on one single carrier substrate before functionalizing them with the respective capture probes. The problem of selectively immobilizing said capture probes on one of two corresponding electrodes which are separated by just a tiny step in the order of few nanometers, experimentally realized were separation layers between 5 and 20 nm, has been likewise recognized to be impossible by means of robotic spotters. The chosen method involves the binding of thiol-functionalized probes to all gold-electrodes, the selective removal by electrochemical stripping and repeated binding of thiol-functionalized probes to the second gold-electrode, and so forth. Each functionalizing requires 2 hours for the binding step alone plus the time which is needed for additional stripping and washing steps. Such method is unsuitable to build complex sensor arrays because it is very time consuming and prone to cross-contamination when once functionalized capture probes must be stripped to obtain pristine surfaces again with all previously bound molecules being physically removed before introducing the new species. This approach suffers from low scalability. Lee and Moon [EP 2088430 A1] presented assemblies of conducting elements like metallic nanowires which were crafted to either one upper or one lower substrate surface. Both such electrode have significantly enlarged nanoscopic surface areas. Here, the upper and the lower electrode carrying the same capture probes, e.g. one antibody. It is intended that the corresponding inserted antibody binds to each of the surfaces separately. It is intended to neither modify the surfaces separately nor to design complex sensor arrays by this method.

Thus, the double sided functionalizing of nanogap capacitor arrays with different biomolecules remains an unsolved issue.

From the state of the art the publications WO 2010/1204479 and EP 2088430 are known. WO 2010/1204479 is direct to a sensor for detecting a nucleic acid molecule comprising an electrode arrangement with two electrodes and nucleic acid probes immobilized at the surface of the electrodes. The present invention also refers to a kit and a method of using the sensor or a sensor array. The present invention is further directed to a process of manufacturing a sensor and sensor array.

EP 2088430 provides a bio-sensor including nanochannel-integrated 3-dimensional metallic nanowire gap electrodes, a manufacturing method thereof, and a bio-disk system comprising the biosensor. The biosensor includes an upper substrate block having a plurality of metallic nanowires formed on a lower surface thereof and including an injection port through which a biomaterial containing sample is injected, a lower substrate block having a plurality of metallic nanowires formed on an upper surface thereof, and a supporting unit supporting the upper and lower substrate blocks so that the upper and lower substrate blocks can be disposed spaced apart at a predetermined distance to form a nanochannel, wherein the metallic nanowires formed on the upper and lower substrate blocks are combined to form three-dimensional metallic nanowire gap electrodes.

SUMMARY OF THE INVENTION

The main objective of the invention is to provide an improved sensor array with surface regions of differently functionalized surfaces and to simplify the process of forming a sensor array with different organic sensor compounds on its surface.

The invention solves this objective by providing a sensor array according to claim 1. The invention further solves this objective by providing a method for producing a sensor array according to claim 13.

The invention refers to a sensor array for the identification and/or quantification of a plurality of target organic compounds, such as biochemical substances and/or nucleic acid polymers, in a mixture of compounds, comprised of or comprising at least two spatially separated functionalized sensor half elements, wherein each sensor half element contains one or more surface regions which are functionalized with one or more sensor compounds each, wherein said sensor half elements are assembled in such a manner that respectively two or more sensor compounds from different sensor half elements are spaced and/or converge and/or contact each other in separate junction areas and wherein said junction areas form a plurality of single sensors for binding to specific kinds of organic target compounds. A plurality of sensor half elements is aligned on or included in or are crafted of one common carrier. The other sensor half elements are aligned on or included in or are crafted of a second common carrier. The surfaces of the sensor half elements are functionalized individually before the assembly of the sensor array.

The invention comprises a new sensor array design which enables the measuring of mixtures, preferably of polynucleotides and -peptides. Each individual sensor consists of one single junction between two surfaces where each of the two surfaces belongs to a different sensor half-element. Each of the two surfaces displays an individual sensor compound which consists of sequences of oligonucleotides, polypeptides or their derivatives like phosphothioate oligonucleotides (PTO), peptide nucleic acids or others.

The difficulty to individually functionalize two surfaces which are less than a micron apart, and foremost to replicate this process with many different sensor compounds to produce an array of many functionalized gaps, leads us to the keynote of this invention. The presented sensor array design enables the manifold presentation of differently modified surface pairs, where the surfaces approach each other at submicron ranges.

All sensitive surfaces of the sensor array were functionalized individually before the assembly the sensor array. Because the surfaces are at first physically separated from each other, it is easy to functionalize the prospective junction areas with single probes. The junction areas are well separated and are modified at each area, e.g. a spot, with only one sensor compound. Immobilizing two compounds as mixture bear the risk of segregating, dimerizing or outcompeting while covalently binding to the surface. The functionalizing with single compounds at lateral clearly spaced sites circumvents those problems. Common techniques like micro contact printing, inkjet printing or the successive photolithographically controlled synthesis can be deployed. One important advantage is that the material of the different surfaces can be identical which allows using the very same surface chemistry for immobilizing the probes. One item which carries one or more functionalized surface areas is a sensor half-element. At least two of such sensor half-elements are required to assemble a complete sensor array.

The invention is also novel over EP 2088430, because the single sensor half elements are not contacted via single lines in that publication. Therefore, the described device is no sensor array at all. EP 2088430 only uses a single sensor compound with which the sensor surfaces are functionalized. For the present invention, however, each single sensor requires at least two different sensor compounds. Thus, the present invention is novel over EP 2088430.

Claim 1 is novel over WO 2010/1204479, because the surfaces of the sensor half elements are functionalized individually and before the assembly of the sensor array. It is therefore possible to provide precisely directed sensor compound layers on the sensor sensor half elements. The sensors of WO 2010/1204479 do not allow such concise separation of the sensor compounds to the sensor half elements. From WO 2010/1204479 it is known that functionalizing the surface of the sensor can be achieved that in a first step the entire surface is completely covered with one sensor compound, that afterwards the sensor compound is removed from parts of the surface, and that in a subsequent step the sensor surface is covered with a further substance. However, this method is prone to carryover impurities of the different sensor compounds. On the one hand, parts of the sensor compounds that shall be removed from the second surface are likely to partially remain on this first surface, so that the compounds mix at the second surface. On the other hand, the sensor compounds functionalizing the second surface may also adhere to free binding sites at the first surface. In general, it is likely that such method leads to misplaced sensor compounds.

By separately functionalizing single sensor half elements on common carriers can any cross-contamination of sensor compounds be prevented, so that the invention provides—in contrast to WO 2010/1204479—the effect to drastically increase the purity of the sensor compounds at the surfaces of the sensors. Therefore the invention is novel over WO 2010/1204479.

By the same reasons, independent claim 13 is novel over WO 2010/1204479. It is emphasized that there are two subsequential steps of functionalizing the sensor half elements when they are separated, and afterwards assembling the sensor half elements, which means bringing the functionalized surfaces together.

WO 2010/1204479 is believed to be the closest state of the art. The difference between WO 2010/1204479 and the present invention is that the surfaces of the sensor half elements are individually functionalized and assembled afterwards. Therefore claim 1 of the invention provides the technical effect, that a more precise sensor can be created and that the fabrication of the sensor is very much simplified. Claim 13 of the invention has the advantageous effect that the fabrication is drastically simplified and a more precise sensor can be fabricated. Compared to WO 2010/1204479 the problem consists in providing a more precise sensor array and providing a simpler method for producing such better defined sensor array. Neither WO 2010/1204479 nor EP 2088430 teach for increasing the precision of the sensor array according to the invention. By using the method disclosed in WO 2010/1204479 a person skilled in the art would not solve the problem of providing a complex sensor array assembly with many differently functionalized electrodes, and where the electrodes are separated by a few nanometers. Such person would build a different kind of sensor using a much more complicated process and would not solve the posed problems due to cross contaminating electrodes with sensor compounds.

A person skilled in the art would further not amend the construction as proposed in WO 2010/1204479 by using a sandwich style sensor instead of a sensor based on one common carrier, because WO 2010/1204479 does not propose to use row elements and column elements arranged on different carrier elements. The assembly of WO 2010/1204479 moreover suggests that the person skilled in the art would use one single carrier and thus excluding the sandwich style approach of the present invention.

It is further not possible for the person skilled in the art to combine the teaching of WO 2010/1204479 and EP 2088430, because there is an evident contradiction between the one-carrier sensor assembly of WO 2010/1204479 and the two-carrier sensor assembly of EP 2088430. A person skilled in the art would not overcome these structural differences, especially because EP 2088430 teaches building a single sensor and not a sensor array.

In order to provide a sensor array having a plurality of single sensors sensitive to different substances, a first plurality of sensor compounds is formed or arranged in surface regions on at least one carrier and a second plurality of sensor compounds is formed or arranged in surface regions on at least one carrier, and each junction area forms one single sensor with a predetermined combination of two or more sensor compounds which are located on two sensor half elements which are spaced and/or converge and/or contact each other.

To increase, structure, group and align the number of sensor half elements on the sensor array and to provide a sensor array that can be produced cost efficiently, the sensor half elements are aligned in a grid structure, with a plurality of row elements and a plurality of column elements, the row elements being formed by a number of sensor half elements and the column elements being formed by a number of sensor half elements, the row elements being aligned and spaced next to each other and the column elements being aligned and spaced next to each other wherein each row element intersects at least one column element in at least one junction area, wherein each junction area forms an individual sensor.

To avoid interferences between neighbouring sensors, it can be provided, that surface regions of sensor half elements are longitudinally delineated and/or separated.

In order to provide a sensor sensitive to a maximum number of different sensor substances, each surface region of sensor half elements is functionalized with a different sensor compound.

To simplify the production and the evaluation of measurement results of the sensor array and to maximise the number of sensors each sensor half element comprises the same number of delineated surface regions.

To increase the stability of the sensor array and to avoid interferences between neighbouring sensor elements at least one or all sensor half elements are made of carrier material or contain carrier material or support a carrier material layer, the carrier material or the carrier material layer being functionalized with one or more of the sensor compounds.

Furthermore, it can be provided, that the carrier materials or the carrier material layers of all sensor half elements are identical. Such a sensor array provides a number of sensors where each single sensor is sensitive to a target molecule which adheres to certain combination of two sensor substances.

To increase the stability of the sensor array, at least one sensor half element or all sensor half elements each comprise a carrier, wherein the respective sensor compound is deposited as a layer on the respective carrier.

To further increase the stability and to simplify the production process, it is preferably provided, that at least one or all sensor half elements comprise or are comprised of a carrier made from a filament, string, wire, band, bar or fibre.

To obtain the maximum number of sensors for a given number of sensor half elements, the number of functionalized surface regions on row elements equals the number of column elements, wherein each surface region of each row element is allocated to and at least partially delimitates or defines one junction area. Alternatively or in addition, it can be provided, that the number of functionalized surface regions on column elements equals the number of row elements, wherein each surface region of each column element is allocated to and at least partially delimitates or defines one junction area.

To enable the appropriate binding chemistry and to provide for the suitable micro environment for the sensor compounds at least one of the sensor half elements, preferably all sensor half elements carry a material layer which is functionalized with a sensor compound.

It can also be provided, that the surface regions of at least one of the sensor half elements, preferably all sensor half elements, are functionalized with sensor compounds and are disjoint or discontiguous. This further reduces the probability of interferences between neighbouring sensor half elements.

To obtain a sensor array, that allows electrical or electronic readout or measurement, sensor half elements comprise electrically or optically conducting carriers or waveguides, wherein the surface regions of the carriers or waveguides are functionalized with the respective sensor compounds, and wherein the electrically or optically conducting carriers or waveguides are made preferably from metal, carbon fiber, conducting polymer or glass fiber.

To avoid shortages or short circuits, preferably when using electrical or electronic readout or measurement, each conducting carrier or waveguide is coated with an insulating layer.

To reduce the use of insulation material, parts of the surface or exclusively only the surface regions of the junction areas are coated with an insulating layer.

To reduce the number of layers and coating steps the insulating layer contains, or is functionalized with, the respective sensor compound.

To increase the sensitivity of the single sensors the insulating layer is covered with an additional layer, preferably made from polymer or gel, which contains or is functionalized with the respective sensor compound.

To obtain single sensors or sensor junctions with equal contact areas the sensor half elements are straight and contact each other in the respective junction area, the junction area preferably being a punctiform region of contact.

To increase the contact areas and the signal sensitivity of the single sensors like the changes in capacitance the sensor half elements are curved and contact each other in the respective junction area, said junction area preferably being a uni-dimensional line or two dimensional curved surface.

To obtain a very homogenous distribution of contact areas the row elements are aligned in a first plane and the column elements are aligned in a second plane, and that the row elements and column elements are arranged in close proximity to or converge to or contact each other in the junction areas.

To increase the stability and the durability of the sensor array it can be provided that all row elements are aligned on or included in or are crafted of one common carrier.

To further increase the stability of the sensor array all column elements are aligned on or included in or are crafted of a second common carrier.

Preferably, the first common carrier and/or the second common carrier are formed as a plate to further improve the stability of the sensor array.

To enable the effective interaction between sensor compounds and target molecules and to increase the sensitivity of the single sensors at least a portion of the circumference of the cross section of the sensor half elements is convex, said cross section preferably being approximately circular or elliptic.

To detect target molecules of different length and to enhance the interaction between sensor compounds and target molecules the gap of the junction area between the sensor half elements is at least partially cuneiform and/or slit shaped and/or said gap comprises a narrowing region.

To further increase the sensitivity of the single sensors, the sensor half elements feature a structured and/or wavelike and/or porous and/or rough surface.

To provide for sufficient gap regions the sensor half elements are arranged on elevations or in cavities of the first common carrier and/or the second common carrier.

To enable efficient molecular interaction between sensor compounds and target molecules it can be provided that within the junction areas the molecules of the sensor compound of the row sensor elements and the molecules of the sensor compound of the column sensor elements are spaced at most in a manner that the organic compounds under investigation or one of its related copies are able to bind to the respective sensor compound arranged on the row elements with a first binding site and to the respective sensor compound arranged on the column elements with a second binding site.

In order to detect organic substances, such as DNA or RNA molecules, the respective sensor compounds of the sensor half elements contain oligonucleotides, binding to binding sites of the target compounds or organic polymers or DNA or RNA molecules.

To detect organic substances having two given binding sites, the respective sensor compounds of the row elements bind to the start sites of organic polymers or DNA or RNA molecules and that the respective sensor compounds of the column elements bind to the end sites of organic polymers or DNA or RNA molecules.

The invention further relates to an advantageous method for producing sensor arrays for the identification and/or quantification of a plurality of target organic compounds, such as biochemical substances and/or molecule sequences, in a mixture of compounds, comprising a first procedure step of functionalizing at least two spatially separated sensor half elements, wherein at least one surface region of each sensor half element is functionalized with one or more sensor compounds each, and a second procedure step of assembling said functionalized sensor half elements in such a manner that respectively two sensor compounds from different sensor half elements are arranged in close proximity to and/or converge and/or touch each other in separate junction areas and where said junction areas form a plurality of single sensors. By using the method according to the invention, a large number of different sensors can be easily produced. The single surfaces of the sensors can be functionalized separately before the sensors are assembled.

To further simplify the production, a first plurality of sensor compounds is formed or arranged in surface regions on a first entity of at least one carrier and a second plurality of sensor compounds is formed or arranged in surface regions on a second entity of at least one carrier, wherein each junction area forms one single sensor with a predetermined combination of two or more sensor compounds which are located on two intersecting or converging or each other touching sensor half elements.

To avoid interferences between neighboring sensors, the surface regions of sensor half elements are longitudinally delineated and/or separated.

In order to obtain a sensor array which is sensitive to a maximum number of different target compounds, each surface region of sensor half elements is functionalized with a different sensor compound.

To increase the stability of the produced sensor array, at least one or all sensor half elements are made from a carrier material, contain a carrier material or support carrier material layer, the carrier material or the carrier material layer being functionalized with sensor compound.

To simplify the production, the carrier materials or the carrier material layers of all sensor half elements are identical.

To improve the sensitivity of the produced single sensors and to detect organic substances having two given binding sites, the distance between two surface regions are equal or smaller than a given distance so that the first binding site of target compound from a mixture of compounds binds to a first sensor compounds of a surface region of a sensor half element of a junction area and that the second binding site of a target compound binds to the other sensor compound of the according surface region of the other sensor half element of the same junction area.

Employing two shorter sequences, e.g. 2 times 5 nucleotides, instead of one sequence of the same combined length of 10 nucleotides, provides for more flexibility in the design of such probes. For example, two shorter oligonucleotide probes parenthesize one longer sequence and can by these means link one very specific site to another distant and much more flexible site. One such site can for example carry the unique exon signature for one gene and the other can address one splice variant specific site.

In contrast to the reaction of two sensor compounds at one single surface, e.g. during bridge amplification, the reaction between two surfaces allows an additional degree of freedom. Molecules have not to bend back to the same surface and amplification can proceed ping-ponging between the two surfaces. If molecules react between two surfaces, those surfaces are preferably arranged in close proximity to each other, which means that the gap between them is within the length of the investigated macromolecules and therefore within sub-micrometer ranges.

After the surfaces of the sensor half-elements have been individually functionalized, the sensor array is assembled through approaching the surfaces towards each other. The gap is narrowed so that both surfaces are close enough to enable the analyte molecules to react with both surfaces, but wide enough to allow the target molecules to enter the gap between both surfaces. Three preferred embodiments are briefly presented without any restriction of the above mentioned invention.

In a first embodiment of the invention, the surfaces are either entirely flat or the sensor half-elements are not allowed to have direct contact to avoid possible electrical shortages or short circuits, then the required gaps are defined through spacers with an effective submicron thickness. The spacers prevent the sensor half-elements from touching each other and is distributed accordingly to provide stability to the sensor half-elements. Position and shape of the spacers are part of the microfluidic layout which directs the analyte and processing solutions through the sensor array.

In a second embodiment of the invention, at least one surface is in parts convexly shaped. Basically, many curvatures are suitable except accurately fitting part-mold setups in the region of the junctions. After functionalizing both surfaces are approached to each other until contact. Because of the geometry contacts occur only in single points, lines or otherwise confined contact areas. At this boundary of the contact areas both surfaces start to separate which defines inevitable an expanding gap. This gap allows for the penetration and reaction of the target molecules. If the sensor half-elements are conductors but do not allow to touch each other as it is preferable for impedimetric sensors to feature an insulating layer.

In a second embodiment of the invention, a polymer coating which forms a loose scaffold and has the probes bound fulfills both functionalities. It separates both carrier cores but allows the target molecules to reach the interface between the functionalized coatings.

By these means the designs enable to build sensor arrays which comprise many different individual sensors.

Interaction of analytes with the paired sensor compounds lead to a change of the physicochemical properties in the gap region, for example an accumulation of the analyte species. In succession signal amplification reactions can be added like PCR, subsequent labeling of the analyte or secondary products. The specificity of the sensor array detection depends on the position of the sensor compounds and not the labeling method. The change of properties in the sensors gap region is used for integral or peripheral signal detection.

The integral signal detection utilizes transmission lines which are part of the support or carrier material of the sensor half-elements. Transmission lines can be either conducting and/or translucent to guide electricity or light. When an energy flux crosses a sensor junction it interacts with the matter in the gap of the junction. For example, if the two surfaces of the sensor are electrically conductive, the gap forms a small capacitor where the kind and amount of the compounds present in the gap determine its dielectric properties. The capacitance is proportional to the effective permittivity, the size of the two adjacent surfaces and inverse proportional to the gap distance. Such impedimetric sensor arrays are able to measuring multiplexed in quasi real-time changes of binding and amplifying of analyte mixtures. The addressing of different impedimetric sensor junctions occurs via the conductive lines and rows of the sensor matrix.

The peripheral signal detection employs external scanning tools to monitor position dependent signals. For example, it is possible to measure light transmission or emission to derive the amount of material in each sensor junction. Here, the sensor half-elements is transparent to allow light interacting with the active interface of the sensor.

BRIEF DESCRIPTION OF THE DRAWINGS

FIG. 13 shows the fluorescence scan of one sensor array half-element after PCR. Background-corrected signal intensities are given for the spots in the framed column.

DETAILED DESCRIPTION OF PREFERRED EMBODIMENTS

Preferred embodiments of the present invention will be described in detail below with reference to the drawings.

Figure 1:
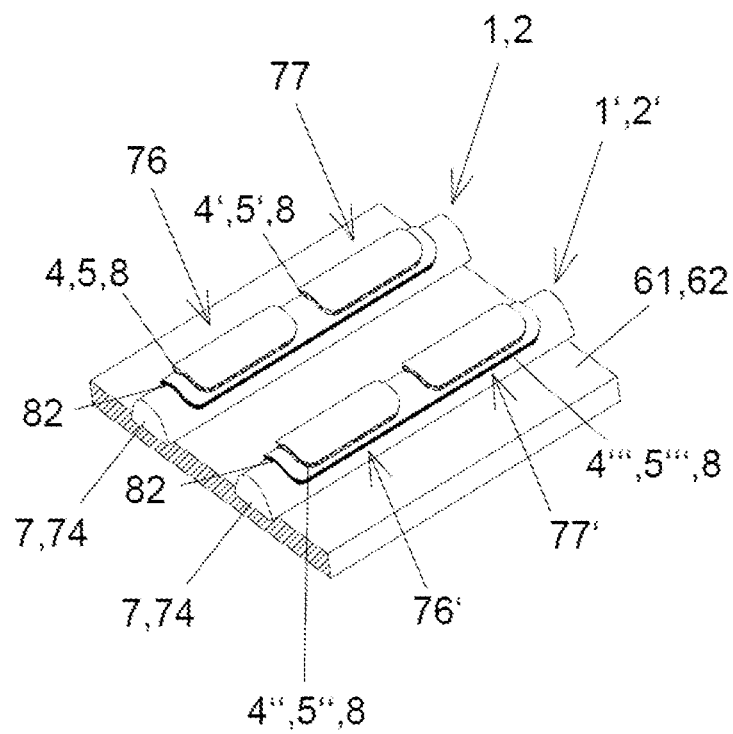
FIG. 1 shows a section of one common carrier with two aligned rounded sensor half-elements and two functionalized surface regions.
Figure 2:
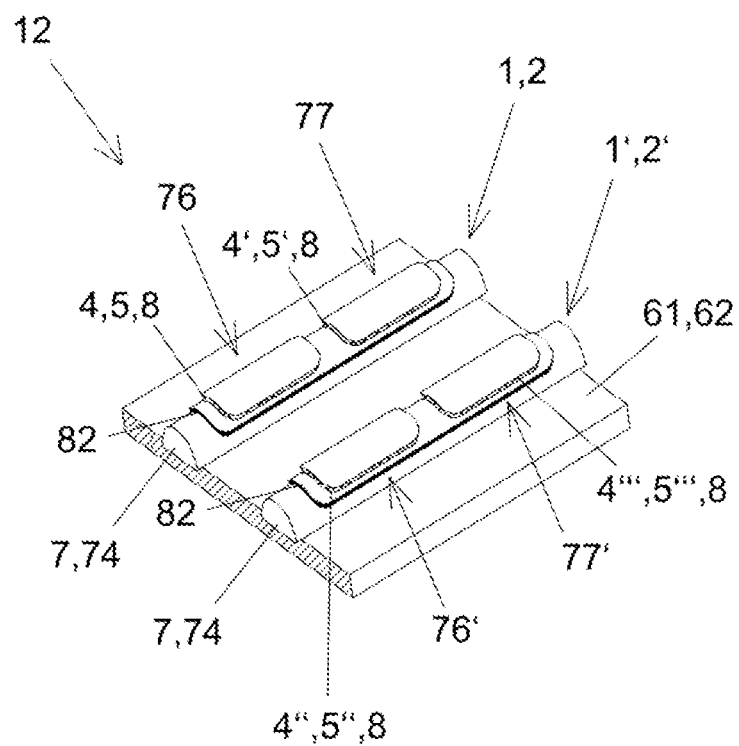
FIG. 2 is an oblique view of a sensor array assembly with two common carriers which support two rounded sensor half-elements each to form four individual sensors.

First Preferred Embodiment: Sensor Arrays with Conducting Sensor Half-Elements which are Supported by Plates and Contain DNA Sensor Compounds The first preferred embodiment is shown in FIGS. 1 and 2 and describes a sensor array 12 with linear conducting sensor half elements 1, 2, which are supported by two common carrier 61, 62 formed by plates. In this preferred embodiment of the invention, the sensor compounds are comprised of or comprise oligonucleotides. The analyte entering the measurement cell (not depicted), which surrounds the sensor array 12, is a mixture of cDNA molecules. The junction areas 31 (cf. FIG. 3) are part of elongated spots, which are arranged along rows and columns of sensor half elements 1, 2. All sensor half elements 1, 2 are arranged in parallel on their respective common carriers 61, 62. One common carrier 61, 62 is depicted in FIG. 1. The functionalization of the sensor half elements 1, 2 occurred before assembling the common carriers 61, 62. During assembly the first common carrier 61 and the second common carrier 62 are approached to each other in such manner that the row and column elements 1, 2 contact each other and are oriented in an angle of 90 degrees as shown in FIG. 4.

The Making of Structured Common Carriers and Sensor Half Elements

The common carriers 61, 62 are made from metal coated silicon wafers using a standard photolithographic process. The preferred design consists of 1000 parallel conductors 74 of 2.5 cm length and 20 µm width which are separated by 5 µm. The individual conductors 74 serve as carriers 7 for the sensor half elements 1, 2. The conductors 74 are arranged on a square shaped area on the respective common carriers 61, 62. The common carriers 61, 62 have an edge length of 2.5 cm. The conductors 74 feature a semi-circular cross-section and have the form of a half cylinder, FIG. 1. The length, width and spacing of the conductors 74 can be easily adapted to the number of sensor half elements 1, 2 and the number of desired sensors 3. The shape of the sensor half elements 1, 2 which are created on the common carriers 61, 62 may alter.

An alternative preferred embodiment comprises trapezoidal conductors 74 with crenated surfaces. In both cases sensor half elements 1, 2 have at least one microscopic convexly shaped surface area at and around the point of contact another sensor half element 1, 2. Accordingly, parts of the surface can be porous or wavelike structured.

The surfaces of the conductors 74 are coated with an insulating thin layer 82 or film by sputtering as part of the photolithographic process that is used for the formation of the common carriers. The sensor half elements 1, 2 are arranged in such manner that the surfaces of the row elements 1 are touching the surfaces of the column elements 2 as shown in FIG. 2. The insulating layer 82 prohibits a direct electrical contact with another conductor 74. The thickness of the non-conducting insulating layer 82 is typically within the submicron range. The insulation layer 82 forms a permeation barrier for electrons and ions. The thickness of the insulating layers 82 of two sensor half elements also determines the closest distance between the conductors 74 and the dimension of the gaps. In this embodiment, the insulating layer 82 is made of polyurethane. Alternatively, it is also possible to use nitrides, oxides and other chalcogenides, self-assembled monolayers, polyelectrolyte multilayers, polymers like polyimides or fluoropolymer-copolymers, electro dipping varnishes, or others known to the art instead. Glass can also be used as insulating coating.

Figure 3:
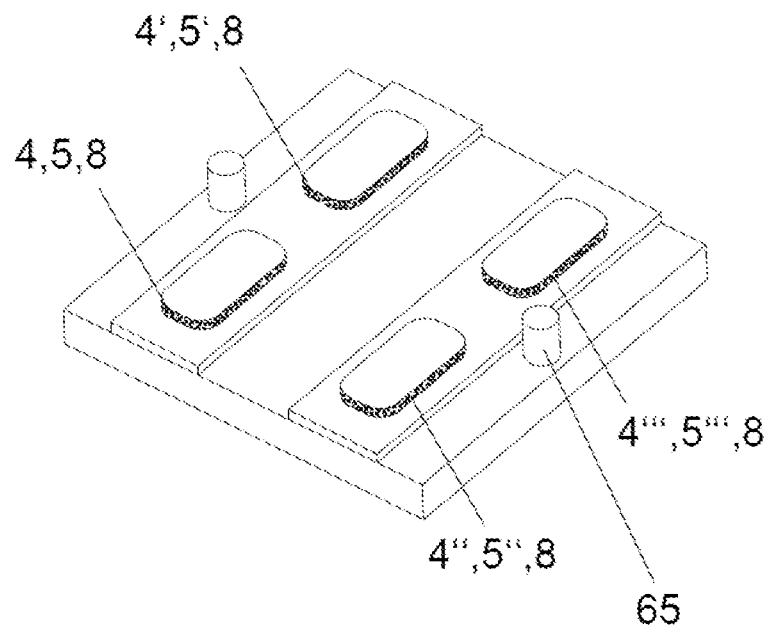
FIG. 3 shows an alternative preferred embodiment of a common carrier with two aligned sensor half-elements, two functionalized surface regions and two spacer elements.
Figure 4:
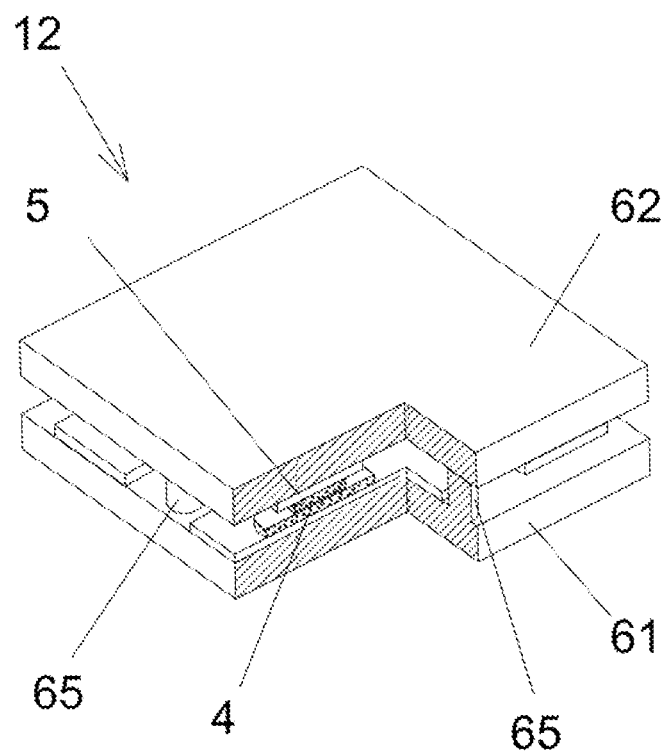
FIG. 4 is an oblique view of a sensor array assembly containing spacers with two common carriers which support two sensor half-elements each to form four individual sensors.

Another alternative preferred embodiment utilizes common carriers 61, 62 with spacers 65 where the spacer elements 65 have been integrated into the common carrier plates 61, 62 as it is shown in FIG. 3. Those common carriers 61, 62 are flat silicon wafer substrates with a pattern of 5.1 μm high pillars as spacers 65. A standard CMOS processes crafts all conductors 74 by physical vapor deposition as 2.5 μm high, 20 μm wide and 10 mm long lines. The center to center distance of the lines is 25 μm. 250 lines are set in parallel covering a total width of 6.25 mm. First, 5 nm chromium undercoating is deposited onto a developed photoresist mask before depositing 2.495 μm gold conductors. After removing the mask a reactive plasma coating process deposits a flat insulating layer of $SiO_2$ 82 above the common carrier 6 including the sensor half elements 1, 2 and spacers 65. Here, the surface of the sensor half elements 1, 2 does not necessarily have to be convexly shaped and can be entirely flat as shown in FIG. 3 because the spacers 65 have a defined thickness and prevent the sensor half elements 1, 2 from touching after completing the sensor array assembly as shown in FIG. 4. The spacers 65 fulfill two functions, namely to firstly create a tiny gap which allows the analyte to enter the gap region and secondly to prevent the conductors 74 from touching each other to avoid short circuits. Even though the passivation and/or insulation of the conductors 74 is possible, those sensor half elements 1, 2 do not necessarily require an insulation layer 82.

The photolithographic process is also used to integrate the addressing or multiplexing units 111, 112 directly into the common carriers. The layout ensures that the conductors 74 are connected to the selection units 111, 112 as schematically shown later in FIG. 9.

Either the carrier 7 itself, the insulating layer 82, or an additional carrier material layer 8 may contain the sensor compounds 4, 5. In the preferred embodiment of the invention, a carrier material layer 8 is applied upon the insulating layer 82. The carrier material layer 8 is able to covalently bind the sensor compounds 4, 5. In the following example, the carrier material layer 8 contains side chains with functional groups which are compatible for cross-linking to appropriately modified oligonucleotides either directly or mediated through an activation reagent. 1-ethyl-3-3-dimethylaminopropyl carbodiimide, EDAC is able to cross-link carboxy groups with amines, glutaraldehyde, bissuccinimidyl esters, diisocyanates or diacyl chlorides cross-link amines with amines, or the formation of thioether cross-links through thiol-reactive groups at amine sites by succinimidyl trans-4-maleimidylmethylcyclohexane-1-carboxylate.

Sensor Compounds

Preferred substances for sensor compounds 4, 5 are oligonucleotides with sequences which are suitable to function as hybridization probes or in particular as primers for solid phase PCR. One preferred class of such sequences has been described in WO2007062445 [Seitz, 2007]. Herein, the oligonucleotides are able to specifically react, which means hybridize and prime, with start and end sites of polynucleic acid analytes 9.

Other preferred classes of sequences are gene and transcript specific primers. For example such sensor array is designed to target blastoma associated gene expression. For this purpose, 84 glioblastoma associated genes with regulated alternative splicing candidates and putative chimeric transcripts, 9 astrocytoma associated intergenic transcriptionally active regions, 33 control regions with housekeeping genes, transcriptionally silent genomic areas, brain and liver associated candidate genes are selected. Genespecific primer pairs are designed for all regions of interest which include several primer pairs per gene, one for each exon and one for each exon-exon junction, which lead to a total of 1794 individual primers. Redundancy which means that certain primers can be used in different primer combinations results in 15507 unique primer combinations. Furthermore, single and, no primer amplification as well as background controls based on non-related genomic regions from mouse and *E. coli* complement the set of sensor compounds. It leads to a total of 15625 primer combinations. Quadruplet repeats bring the total of sensor junctions 31 to 62500 which corresponds to 250 row and 250 column sensor half elements. It represents $\frac{1}{16}^{th}$ of one larger sensor array with 1000×1000 sensor half elements. All primers are designed to comply one melting temperature Tm of 62±0.5° C. The primers contain 21 to 29 nucleotides and have no homopolymeric stretches exceeding three consecutive nucleotides. The primers contain a 5'-amino group modification to be able to covalently bind to the solid support.

Functionalization of the Sensor Half Elements

Figure 5:
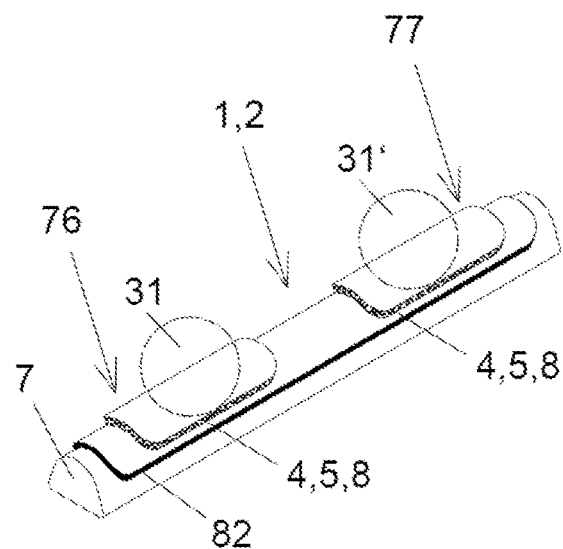
FIG. 5 shows an alternative preferred embodiment of a sensor half-element and its cross-section with one insulating layer and two carrier material layers which contain the sensor compounds.

The sensor compounds 4, 5 are immobilized to the surface of the carrier material layer 8 by covalent binding to the surface via cross-linkers which were described above. One separate sensor half element 1, 2 is depicted in FIG. 5. It consists of a carrier 7, which is covered by an insulation layer 82 and material layer spots 8 which contain the sensor compounds 4, 5.

The sensor half elements 1, 2 are either functionalized separately or alternatively, the sensor half elements 1, 2 are assembled on common carriers 61, 62 and functionalized afterwards in groups which are determined through the assembly on the common carriers. However, before the common carriers 61, 62 are approached the sensor half elements 1, 2 are functionalized on the respective common carriers 61, 62. If the carriers 7 of the sensor half elements 1, 2 are narrowly spaced on the respective common carriers 61, 62 before functionalization, the functionalization feature a precise lateral resolution of the same dimensions as the sensor half element assembly. In order to obtain such lateral resolution, three technologies fulfill those requirements.

Firstly, standard piezo plotters with spot sizes at around 20 µm are able to deposit the sensor compounds 4, 5 from diluted solutions, e.g. 20 µm, onto the respective positions of the carriers 7 which are covered by the insulating layer 82 and material carrier layer 8. Printing is followed by incubation at constant humidity and elevated temperatures, e.g. 60° C., which facilitates the covalent binding to most of the available binding sites. Afterwards, any surplus sensor compounds 4, 5 which have not reacted are removed by flushing with blocking and washing solutions. As a result, the localized areas of the sensor half elements 1, 2 are covered with dense material carrier layers 8 containing the dedicated sensor compounds.

Secondly, for line widths below 50 µm DNA probes can be directly synthesized or on the surfaces of the respective carriers 7. This process is directed by photolithography and uses photo-activatable linkers. It is already a standard technology in microarray production. Only the sensor substances 4, 5, e.g. partial sequences of the DNA probes which are specific to the individual sensor half elements 1, 2 have to be synthesized at the surface. Common sequence motifs of the sensor compounds 4, 5 can be synthesized beforehand in bulk syntheses and immobilized to the insulating layer 82 or carrier material layer 8. Such pre-cursor compounds can be applied unison to many or all carriers 7 at once. Alternatively, it is also possible to modify all or groups of sensor half elements 1, 2 with precursors before the remaining nucleotides are synthesized step by step in situ. The individual nucleotides can be deposited using microcontact stamps. Because the genetic code contains four different bases only four different stamps are required for one additional nucleotide position. Each reaction is followed by a washing and activation cycle. It is also possible to immobilize a series of precursors, e.g. 64 which contain three selective nucleotides already. Afterwards, only a reduced number of additional selective nucleotides is synthesized in situ at the surface.

Thirdly, stamps which contain microfluidic channels are filled with the respective compounds 4, 5. For instance, the stamps contain 64 channels. 16 such stamps comprising 64 channels respectively are used in line to modify up to 1024 sensor half elements 1, 2. This method is advantageous if entire sensor half elements 1, 2 are modified with the same sensor compound 4, 5.

For example, the entire surface of the common carrier plates 61, 62 including the rows and columns of conductors 74, which have been protected by the insulating layer 82 $SiO_2$, are activated by immersing the surfaces in silanization solution of 3% 3-(glycidyloxypropyl)trimethoxysilane in 95% ethanol. The silanization produces a homogeneous reactive layer which is stabilized through moderate baking at 110° C. Such activated surfaces can be stored under inert gas or in vacuum.

A number of 897 primers of the above example are spotted using a piezo printer to each common carrier 6 along the lines of sensor half elements 1, 2 in a pattern of randomly distributed triplicates. The spotting layout for both common carrier plates 6 match the desired primer pairs in the finished assembly. Forward and reverse primers are distributed to the sensor half-elements 1, 2 on both common carrier plates 61, 62. The diameter of a single spot is 20 µm, the pitch is 25 µm, and 250×250 regular spots are set into a square format. The covalent binding proceeds in a humidity chamber over night at 25° C. Not reacted molecules and spotting buffer are removed through immersion in blocking solution of 50 mM ethanolamine and/or 100 mM Tris at pH 9 for 15 minutes followed by thoroughly rinsing the surfaces with water.

Alternatively, it is possible that another insulating layer 82 is directly functionalized with the sensor compounds 4, 5. Such an embodiment of the invention does not contain an additional carrier material layer 8. The insulation layer 82 itself binds or contains the sensor compounds 4, 5. Further alternatives are that the sensor compounds 4, 5 can be embedded or bound to the carrier material layer 8 during the coating process, e.g. when the insulating layer 82 is coated with the carrier material layer 8. However, sufficient amounts of sensor compounds 4, 5 remain accessible at the surface.

In the preferred embodiment of the invention all sensor half elements 1, 2 are made from the same basis material and each of the used carriers 7 or conductors 74 can be individually modified using the same chemistry. The sensor half elements 1, 2 are processed separately in order to ensure that the sensor compounds 4, 5 remain physically separated during their immobilization. Alternatively, it is also possible to use different basis materials and/or different binding chemistry. For instance, different organic molecules like amino- or carboxy-compounds can insert different lateral spacers at the surface of row elements 1 and column elements 2 to design junction areas 31 with defined surface charge asymmetries.

Figure 6:
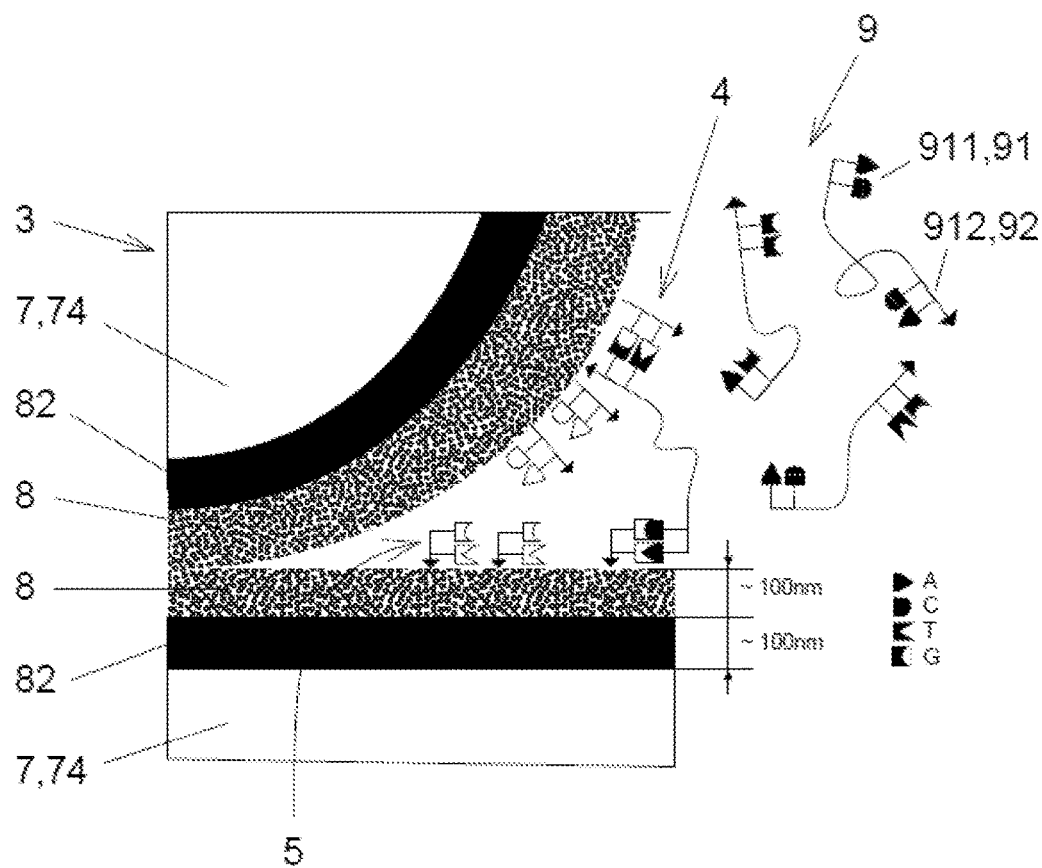
FIG. 6 shows the schematic cross-section of one junction which is formed through the shape of the sensor half-elements with the principle reaction scheme of dual hybridization reaction.
Figure 7:
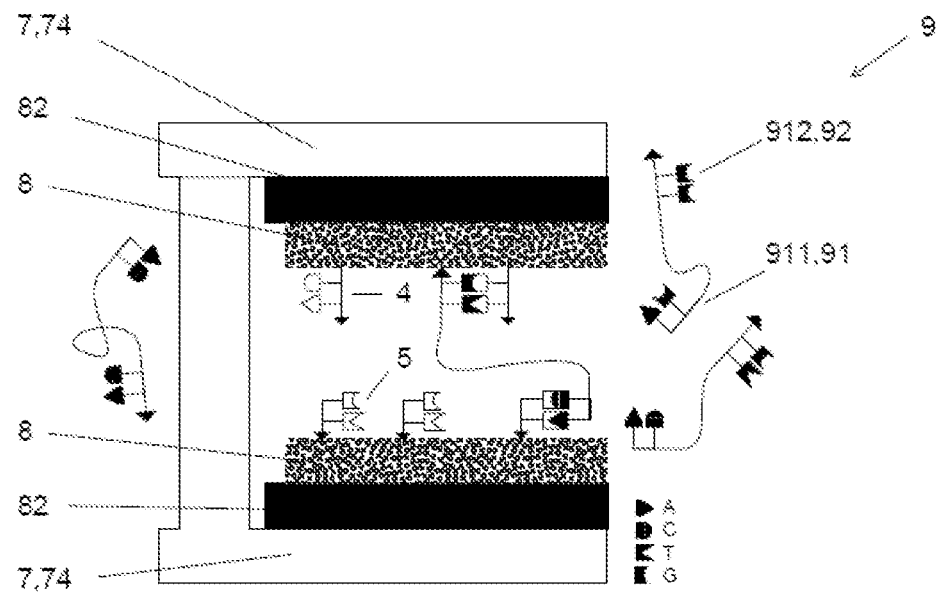
FIG. 7 shows the schematic cross-section of one junction which is formed through distance spacers with the principle reaction scheme of dual hybridization reaction.

Assembly of the Two Sensor Half-Elements to One Sensor Array and Measurement Cell Each of the sensor half elements 1, 2 on the common carriers 61 are prepared in the above mentioned manner. Afterwards, the common carriers 61, 62 are assembled to the sensor array 12 which has the form of a cross network as shown in FIG. 2 or 4. Both common carrier plates 61, 62 with the sensor half elements 1, 2 are stacked in such way that the sensor half elements 1, 2 located on opposing common carriers 61, 62 face each other, whereby each two sensor half elements 1, 2 facing each other are oriented perpendicularly. The spacers 65 in FIG. 4 ensure a defined gap of 100 nm between the two sensor half elements 1, 2 for each junction 31. Each junction 31 constitutes one individual sensor 3. Schematic close-ups of the formed junctions are shown in FIGS. 6 and 7. The figures do not represent the correct spatial relationships between the conductors 74, which have cross-sections of one to several µm, whereas the coatings are in the submicrometer range, the exemplary molecular sensor compounds 4, 5 and analytes 9 such as DNA molecules. The latter typically have an average length of 2500 nucleotides and are approximately 0.85 µm long.

The assembly becomes embedded into a cartridge enclosure which provides microfluidic connectors, sealing along the edges, electric and thermal contacts to the carrier plates.

Molecular Recognition

The basic principle of the sensor action is a molecular recognition reaction between the analytes 9 under investigation and the sensor compounds 4, 5. Different kinds of reactions are possible, for example:
  a. hybridization FIG. 6 and FIG. 7,
  b. hybridization and amplification FIG. 8.

Figure 8:
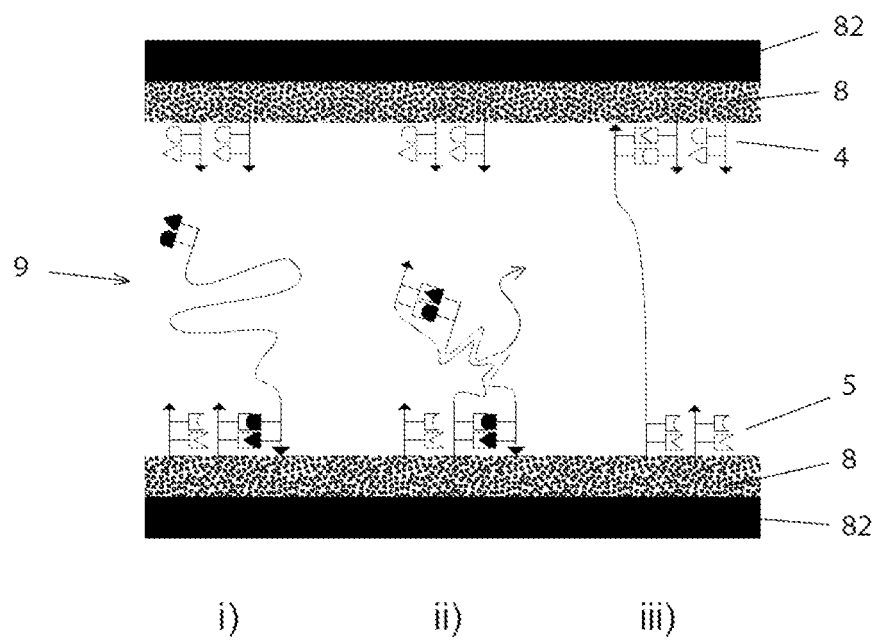
FIG. 8 shows the schematic cross-section of one general junction of sensor half-elements with the principle amplification reaction scheme.

FIGS. 6 to 8 show schematic representations of the reactions a and b. The symbols indicate a certain nucleotide adenine, A, thymine, T, guanine, G or cytosine, C which are able to match the complementary nucleotide, A with T and G with C. The filled symbols represent the analytes whereas the hollow symbols stand for the sensor compounds or reaction products. The arrows indicate the 5' towards 3' direction of the oligo- and polynucleotides.

a. Hybridization:

Sensor 4, 5 compounds are oligonucleotides which are immobilized either with their 5'-site at one group of sensor half elements, e.g. at all row elements 1 shown as the top element in FIG. 6, 7, or with their 3'-site at the opposite column elements 2 shown as the bottom element in the same figures. Molecules of an analyte mixture 9 of e.g. cDNA which enters the sensor array are able to hybridize to the sensor compounds 4, 5 as shown in FIG. 6, 7. Analytes hybridize at the 3'-, 5'-, both or non sites. The hybridization buffer, containing e.g. de-ionized formamide, Denhardts, Tween, SDS, dextran and DEPC, the temperature and time are optimally chosen for sequence specific dimerization and trimerization. Such conditions are based on the primer design e.g. 62° C. and 1 h. During this period the solution is agitated to accelerate diffusion rates into the surface of the gap regions. The final hybridization is the equilibrium binding state. Not hybridized polynucleotides can be removed through washing steps. The result is a segregated analyte pattern in the sensor array.

The sensor compounds might contain a position lock, which means that sequences extensions of analyte and the sensor compounds allow hybridizations only at the start 911 or end 921 of the analytes. The consequence is that short sequences of 1 to 8 nucleotides can be used to obtain an efficient segregation. For illustration, each longer analyte nucleotide sequence has anywhere in their chain at least one A, but only in average one quarter starts with one A. This principle applies to each nucleotide position.

b. Hybridization and Amplification:

Sensor compounds 4, 5 are primer oligonucleotides, which are immobilized with their 5'-site as shown by sketches in FIG. 8.

In a first step i) in FIG. 8, polynucleotides of the analyte mixture 9 entering the sensor array 12 and hybridize only to those primers 4, 5 which are complementary to their 3'-side. The hybridization buffer contains deionized formamide, Denhardts, Tween, SDS, dextran and DEPC, the temperature and time are optimally chosen for sequence specific hybridization, based on the primer design for example 62° C. for 1 h. During this interval the solution is agitated to accelerate diffusion rates into gap regions. Non-hybridized analytes 9 can be removed by washing.

In a second step ii), an assay with activated polymerase like Taq, Pfu, Phusion or similars, single nucleotides dNTP's and additives such as divalent cations and stabilizers are applied to perform a single elongation 70° C. for 2 min. The reaction results in bound complementary copies of the analytes 9 at the sensors 3 according to the sequence and proportional to the starting concentration. Stringent washing denatures the dsDNA and the original template can be removed leaving the covalently bound complementary sequence at the sensor array 12.

In a third step iii), a fresh assay with polymerase, dNTP's and additives will be inserted and a controlled polymerase chain reaction is performed through thermocyling, e.g. 50 cycles of 95° C. for 30 sec, 62° C. for 30 sec and 70° C. for 2 min. Only those polynucleotides which find complementary primers at the opposite surface can be amplified. The amplifications proceed alternately between the opposite surfaces in the gap regions.

The hybridization method, a, is simple because no additional enzymatic reaction and no fast thermocycling is required. The hybridization and amplification method, b, is technically more sophisticated but provides two advantages. First, the proof-reading function of the polymerases introduces corrections for mispriming events. Second, the amplification multiplies the amount of analyte 9 in the junctions 31 through the generation of identical copies.

The biochemical molecular recognition fulfilled the first part of the sensor reaction. It detects and segregates the analyte 9 into different subpools. It means that each sensor 3 contains predominantly sequences which correspond to the sensor substances 4, 5 of both sensor half elements 1, 2 facing each other. A real time or endpoint measurement can only identify the amount but not the kind of material in each sensor 3. With regard to subsequent electrical characterizations further signal enhancements can be achieved through post labeling with materials which possess strong interaction with alternating electric fields for example conjugated polymers or metallic nanoparticles.

Sample Preparation and Sensor Array Processing

The primary sample can be RNA extracted from a tissue which has been obtained by biopsy. At the time of sampling, the tissue has been immersed immediately in RNAlater which is an aqueous storage reagent that rapidly permeates tissues to stabilize and protect cellular RNA. A kit is used to generate cDNA as secondary sample through reverse transcription, RNA digestion and purification. In this process is the sample can be modified through sequence extensions which enable primers to lock into respective start and end site positions.

The processing follows the above described principle. For the hybridization and amplification assay a minimum of 1 μl of cDNA sample and PCR master mix which includes dNTP mix, polymerase, buffer and additives, is injected via the microfluidic ports into the gap between the sensor half-elements 1, 2. Heating for 30 sec to 94° C. melts and unfolds any hybridized polynucleotide stretches and activates the polymerase. The initial hybridization phase, i) in FIG. 8, just above the annealing temperature of the given example, 62° C., enables the cDNA templates, shown with black filled symbols in FIG. 8, to bind to the corresponding sites at the sensor compounds, shown with hollow symbols in FIG. 8. One elongation step for 1 minute at 74° C. generates surface bound complementary copies of the analytes, ii) in FIG. 8. The following denaturing step, 30 sec at 94° C., and washing step removes any analyte molecules, which is symbolized in step ii of FIG. 8 through the dashed line of the cDNA template and the arrow which indicates that those molecules leave the system. During the subsequent annealing phase, 30 sec at 62° C., hybridize surface bound analyte copies with sensor compounds at the opposite sensor half element surface, iii) in FIG. 8. Only those molecules are able to amplify during the next PCR cycles. A minimum of 1 μl fresh PCR master mix is injected. PCR is performed over 50 cycles. The DNA concentration increases with each cycle in those junctions where analyte molecules with end sequences compatible to both sensor compounds 1, 2 have bound during the first hybridization phase.

Measurement

As the carrier of the sensor half elements 1, 2 is conductive each junction 31 can be electrically addressed through both of the connecting sensor half elements 1, 2. The measurement of amplified DNA at each junction 31 is performed by impedance measurements either after each cycle at constant temperature or as endpoint measurement. The junction areas 31 act as capacitors which are able to sense the dielectric properties of the compounds in the gap region or the sensor 3. Each junction area 31 can be envisaged in a first approximation as a parallel alignment of tiny plate capacitors of different width and area which enclose small partial volumes adding all up to the total active surface and volume. The detection of the capacitance occurs through sending a timely variable electrical signal, e.g. voltage steps and pulses, AC potential or current, along one conductor and recording the response at the other conductor.

The relative permittivity of DNA solutions changes in a concentration dependent manner from pure water with a relative permittivity, $\in_r$ of 80 to over 90 for a 1% DNA solution. Those values have been measured for example at 1 MHz by Takashima [1984]. In contrast, air has a $\in_r$-value of 1 whereas typical organic polymers range between 6 and 10. This implies that double-stranded DNA strongly alters the dielectric response of the sensor junctions. Impedance changes are recorded during the measurements. The results of the measurement are quantified during the measurement series and the data analysis recalculates the concentration ratios of the analyte molecules 9 in the original sample. In first approximation, each sensor 3 can be envisaged as a parallel alignment of tiny plate capacitors of different width and area, which all add up to the total active surface area and volume. For example, a 50 μm conductor 74 junction 31 forms a total cross-section of $2.5 \cdot 10^{-9}$ m$^2$. With an insulating layer 82 of 0.1 μm thickness, the minimal separation of both sensor half elements 1, 2 is 0.2 μm. Using the following equation with 10 equal steps and $\in_r$ of water with 80, the total capacitance approximates to 192.1 fF.

$$C = \sum_{i=1}^{n} \varepsilon_0 \varepsilon_r \frac{A_i}{d_i}$$

Assumed that the most inner part of the junction 31 is defined through the first 10$^{th}$ of the distance and area changes its dielectric properties due to an accumulation of DNA following above described molecular recognition reactions. If $\in_r$ of this section changes from 80 to 90, the capacitance increases to 200.3 fF.

Figure 9:
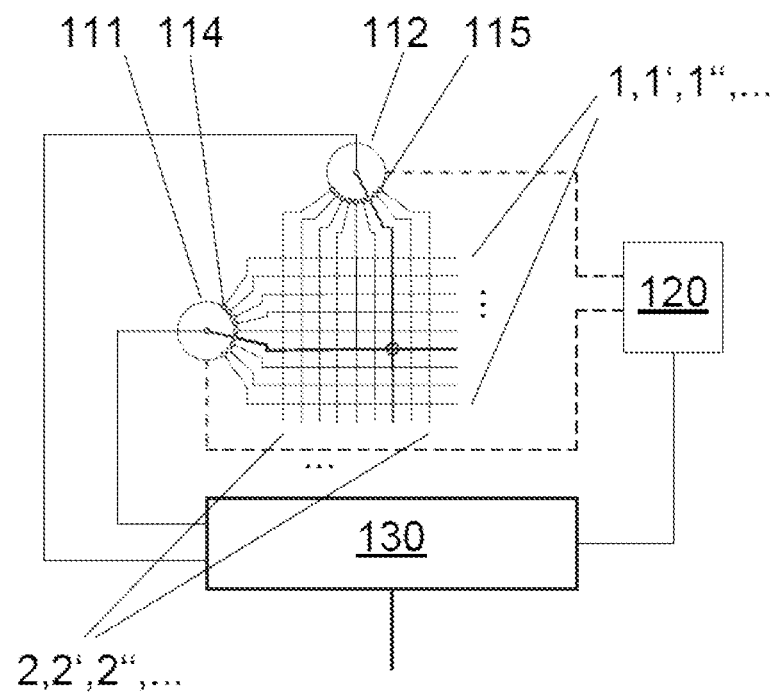
FIG. 9 shows the evaluation circuit for the electrical detection of the concentration of the compounds under investigation.

FIG. 9 shows the evaluation circuit 100 comprising a first selection unit 111, e. g. an analog multiplexer, with one primary port and a plurality of secondary ports 114 which are individually connected to one row element 1 each, a second selection unit 112 with one primary port and a plurality of secondary ports 115 which are individually connected to one column element 2 each. The circuit 100 further comprises a control circuit 120 which controls the two selection units 111, 112. The first selection unit 111 selects one of the row elements 1 and the second selection unit 112 selects one of the column elements 2. The measurement circuit 130 quantifies the electrical impedance between the main ports of the addressing circuits 111, 112. Each combination of a column element 2 and a row element 1 enables one distinct sensor 3 formed between the respective selected sensor half elements 1, 2. The impedance of the addressed sensor 3 is measured by measuring the impedance between the primary ports of the selection units 111, 112. Sensor half elements 1, 2 next to the addressed combination of sensor half elements 1, 2 are held or fixed to a constant potential, e.g. floating ground. All sensors 3 are measured in consecutive or any other order. It is possible to analyze several sensors 3 in parallel by addressing one row sensor half element 1 and several column sensor half elements 2, and vice versa, by employing a number of further selection units 111, 112 and measurement circuits 130.

In this preferred embodiment of the invention, the measurement unit 130 is a combination of potentiostat and frequency analyzer that records amplitude and phase shift of the response signal in comparison to the entrance AC signal. Impedance spectra can be used to characterize the substances being bound to the respective sensors 3. Oscillator, charge and AC bridge based approaches are in use to determine capacitances, whereby the charge based capacitance measurement technique, CBCM, is the simplest realization. AC bridge based commercial instruments and circuit designs are available to measures capacitances with 1 fF resolution but potentiostats have been presented to approach the 10 aF range [Carminati, 2009]. It might be not always necessary to determine capacitances or impedances through modulus and phase shift. Under equilibrium conditions both readings can be transformed into each other. Furthermore, if a phase shift is seen to be known it might be enough to determine the modulus and calculate the capacitance using a valid equivalent circuit. By these means is it possible to use single frequency measurements to determine valid capacitances.

The impedance or capacitance is either determined by end point measurements or by using real time measurement. Real time measurements are able to characterize the temporal behavior of the electrical properties of the sensors during the molecular recognition reactions. Real time therefore enables to follow hybridization kinetics and amplification rates during thermocyling depending on the type of experiment. For endpoint measurements is it advantageous to wash the sensor array with pure water and also measure in pure water or under dry conditions. It reduces the crosstalk between neighbouring sensors 3.

Figure 10:
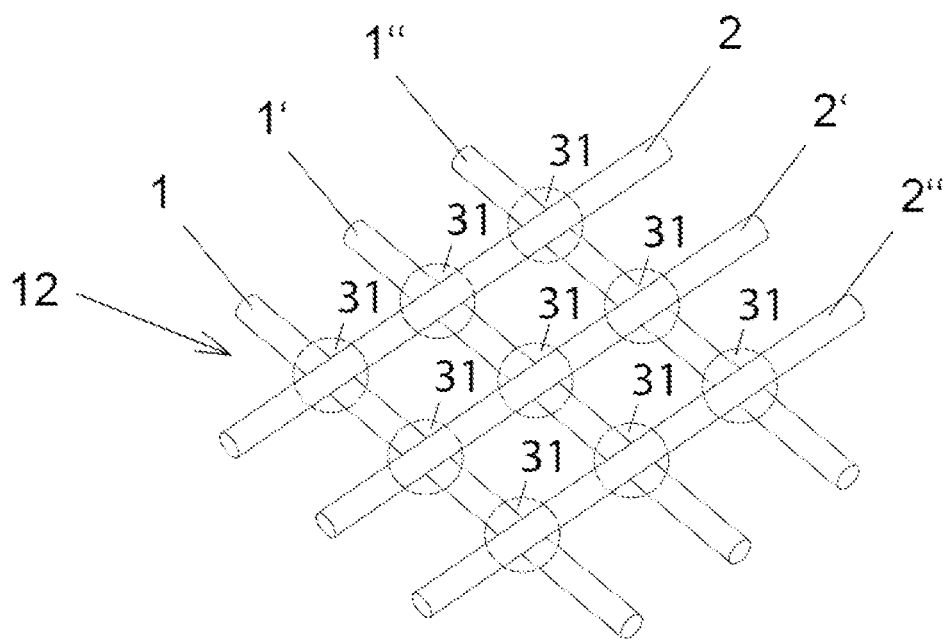
FIG. 10 is an oblique view of a network with numerous straight aligned sensor half-elements.
Figure 11:
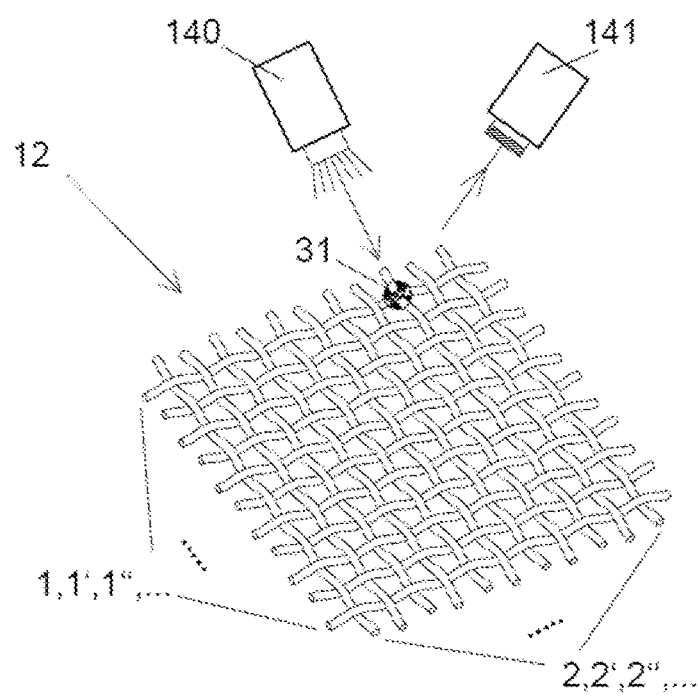
FIG. 11 shows one measurement method for determining the concentration of the segregated analyte with a light source and light detector unit.

Second Preferred Embodiment: Sensor Arrays with Transparent Sensor Half Element Glass Fibers and Polypeptide Sensor Compounds The second embodiment of the invention describes a sensor array 12 with straight aligned sensor half elements 1, 2 as shown in FIG. 10 or woven sensor half elements 1, 2 as shown in FIG. 11 which are grouped as row 1 and column elements 2. All sensor half elements 1, 2 are identical except their individual functionalizations. The gap between the sensor half elements 1, 2 is caused by the convexly shaped surface of the sensor half elements 1, 2. The sensor half elements 1, 2 are transparent. An optical readout device 141 detects changes in the gap area 31 of the individual sensors 3. The sensor compounds 4, 5 are polypeptides and polynucleotides. The analyte 9 are polypeptides.

Sensor Half-Elements and their Functionalization

Commercially Available Glass Fibers of 20 μm Outer Diameter were Chemically Activated by silanization to produce amino-reactive layers with N-hydroxysuccinimide, NHS activated moieties in a batch process.

Twenty antibodies like anti-TBP mAb and anti-CREBBP mAb which are directed against known human transcription factors were covalently bound to the NHS surfaces of the glass fiber carriers. For this purpose, a relief printing plate has been made from standard photopolymer printing resist with 20 μm broad elevated lines which were charged with solutions of said antibodies in immobilization buffer at approximately 1 μg/μl. The antibodies serve as sensor compound 4 and are shown as Y-shaped symbols in FIG. 12. The deposition of antibodies in the designated areas along a first batch of fibers has been achieved by contacting activated fibers and the printing plate in perpendicular orientation relative to the elevated stamp profile. The fibers were incubated until the binding reaction has completed. Subsequent hydrolysis of non reacted NHS-ester affects the unmodified stretches of the glass fibers to be hydrophilic. As consequence, functionalized fiber areas are interspersed by hydrophilic but unmodified regions. Fibers are at least 1 cm long and can be stored until device assembly.

A second batch of fibers is modified using a selection of presumed DNA sequences responsible for transcription initiation. The sequences include regions upstream of transcription start sites and a 5'-amino modification. The sequences serve as second sensor compounds 5, were also immobilized by covalent to NHS-activated glass fibers as described above and are shown as double line in FIG. 12.

Assembly of the Sensor Half Elements to One Sensor Array and Measurement Cell

The sensor array 12 comprises the entirety of all individual junction areas 31. For practical reasons such as adding the mixture of target compounds or flushing the sensor array with washing buffer such sensor array 12 is supported and/or encapsulated by a frame, chamber, cartridge or other kind of enclosure. Such assembly constitutes the measurement cell. Measurement cells are preferably manufactured from polycarbonate.

The sensor half elements 1, 2 are modified fibers featuring a length of some centimeters that are mounted to the cell void at designated places. A robotic mini-loom assembles the row sensor half elements 1 from the first batch carrying antibodies and the column sensor half elements 2 from the second batch with DNA into a woven mesh like structure as shown in FIG. 11. The correct positional alignment of the sensor half elements 1, 2 or modified fibers is facilitated by tracking co-deposited dye in the functionalized fiber segments or segments of the sensor half elements 1, 2 during assembly. The polycarbonate cell is transparent, encapsulated and contains mircofluidic ports.

Sensor Array Processing, Measurement and Read Out Device

Filling of the fiber sensor array occurs via feeder and drain channels, connectors and vents. Fluorescence signals are read by a coupled fluorescence microscope. Absorbance measurements are carried out by coupling the optical paths to via fibers to a spectrophotometer. The glass fibers forming the carrier of the sensor half elements 1, 2 focus the optical path at individual junctions 31 which leads to an increased signal-to-noise ratio.

Figure 12:
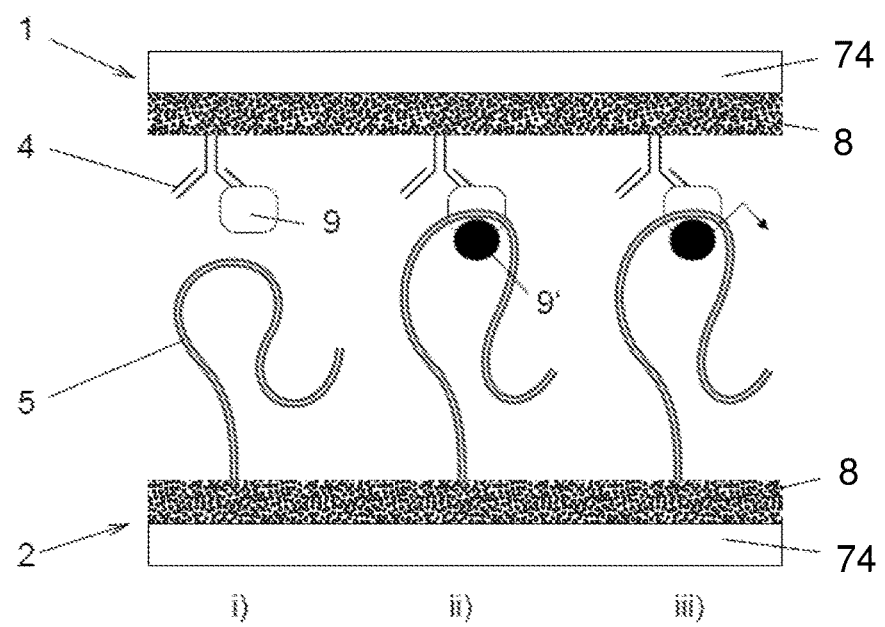
FIG. 12 shows the schematic cross-section of one general junction of sensor half-elements with the principle reaction scheme of an antibody—DNA-enhancer screening array.

At the beginning of each experiment a baseline scan of the sensor array 12 is recorded before the cell is filled with a solution containing a mixture of transcription factors, the analyte 9, white square shaped symbols in FIG. 12. The transcription factors are captured by the immobilized antibodies at the row sensor half elements 1, i) in FIG. 12, and interact with column bound DNA fragments to form DNA-protein complexes. After a low stringent washing step another optical scan quantifies the amount of protein which has been captured by the individual sensors in the sensor array. Then, a second analyte 9 sample solution with enhancer proteins is injected and coordinates with the formed DNA-protein complexes, ii) in FIG. 12, black disks. Finally, an in-vitro transcription is carried out using RNA-sensitive fluorescent dyes or fluorescent labeled nucleotides, iii) in FIG. 12. The continuous observation of signal derives kinetic information on transcription factor, enhancer and DNA-sequence interdependence and results in transcription initiation efficiency.

Alternatively, whole cell extracts can be used instead of purified enhancer proteins. The efficiency changes are quantified to conclude the transcriptional state of the analyzed cells.

Further Embodiments

In the following, alternatives and variations of the invention are described.

Sensor Half Elements with One Sensor Compound

The preferred embodiments above describe sensor half elements 1, 2 which hold sensor compounds 4, 5 at localized junction areas 31. Those sensor compounds can differ of course. However, it is also possible that each sensor half element 1, 2 contains only very few or even just one sensor compound 4, for example one forward primer 4 or one reverse primer 5. This embodiment implies the following two features.

Firstly, the number of different sensors compounds 4, 5 on the sensor half elements 1, 2 increases linearly while the number of different unique sensors 3 increases quadratically. In our example, each combination of one forward primer 4 with one reverse primer 5 leads to one unique sensor, and therefore the combination of m forward primers 4 and n reverse primers 5 results in m×n unique primer combinations and sensors 3. This combinatorial sensor design principle minimizes the need for extensive primer libraries.

Secondly, each sensor half element 1, 2 only needs to be coated with one sensor compound, which lowers the requirements for the deposition methods of spotting or micro contact stamping. Position accuracy is less important along each sensor half element, because large parts of the whole surface of the sensor half element 1, 2 is covered with the respective sensor compound 4, 5. The coating of fibers or wires can also occur entirely without spatially resolved deposition methods. Such sensor half elements 1, 2 can be functionalized in a batch process before assembling the sensor half element 1, 2 to the respective common carrier 61, 62.

Conducting Sensor Half Element Fibers

The first preferred embodiment describes conductive sensor half elements 1, 2 and in particular the electrical measurement of the individual sensor 3. The second preferred embodiment describes the functionalization and the assembly of fiber sensor half elements 1, 2 which are not supported through a common carrier 6. According to the first and second preferred embodiment of the invention, the carriers 7 are conducting wires 74 made of metals like copper, gold or suitable alloys having the same or higher electrical conductivity. As for a high degree of integration thin and long conductors are required, high specific conductivities are advantageous to obtain an acceptable conductivity of the sensor half elements 1, 2. Sensor half elements 4, 5 have an insulating coating 82.

According to a first alternative of the invention, the carriers 7 are made from aluminum wires with thicknesses on the order of 10 to 50 μm being anodized to form an insulating layer 82. Current density, time and the anodizing solution determine the density and thickness of the oxide layer. Then, through the reaction of organosilanes such as 3-aminopropyltrimethoxysilane or N-2-aminoethyl-3-aminopropyl-trimethoxy-silane with hydroxyl groups, which have formed from the most outer oxide layer in aqueous phase, amino functionalization is introduced. This allows for the binding of appropriate oligonucleotides or -peptides trough cross-linking reactions as described above.

According to a second alternative of the invention, the carriers 7 can be made from carbon fibers being chemically oxidized at the surface to gain a high density of carboxyl groups. Those carboxyl groups are able to react with transient activation reagent like EDAC. Amine modified oligonucleotides can be cross-linked afterwards to form an impermeable interface between the carbon fiber and the oligonucleotides or -peptides.

Examples: Sensor Half Elements Surface Structuring

The extent of surface interaction can be enhanced through additional soft matter coatings which are grouped in the category carrier material layer 8. Polymers, in particular gels, are suitable to form a coating which can be squeezed. Such coatings contain binding sites to covalently bind the sensor compounds 4, 5. The junction area 31, i. e. the region between two sensor half elements 1, 2 where molecules 9 under investigation can bind to each of the sensor compounds 4, 5 with two of its binding sites 91, 92, can be increased by using said gels. Dendrimers like polypropylenimine polyamine range from tetramines to tetrahexacontamines and can be chosen to build 3D-like structures with higher interface densities of the sensor compounds 4, 5.

FIG. 5 presents a sensor half element 1, 2 which is supported by a carrier 7 and coated by an insulating layer 82. The different sensor compounds 4, 5 are embedded in a carrier material layer 8 and are applied in separated regions or areas 76, 77. The position of the junction areas 31 is defined by the position of the separated areas 76, 77 of the sensor half elements 1, 2. The areas should be kept as small as possible without compromising the size of the sensor area which can be connected through the analyte molecules 9. The minimized design combines two advantages. First, less sensor compounds 4, 5 are required to produce the individual senor half elements 1, 2. Second, the surface regions outside the junction areas 31, where the analyte could be trapped without contributing to the measurement, are minimized.

As a consequence, the active surface is present in the junction area 31 only.

One alternative to the spatial resolved modification of sensor half elements 1, 2 is to coat and immobilize large areas of the sensor half elements 1, 2. Afterwards the layers at regions outside the junction areas 31 are stripped. Light can be used to trigger a release reaction outside the shielded junction areas 31 when using a photolabile linker to immobilize the sensor compounds 4, 5.

Example: Increasing the Signal-to-Noise Ratio

In addition to standard weaves, which are made of regular warp and weft patterns, structures can be formed in which pairs of sensor half elements 1, 2 cross each other several times. Alternatively, it is also possible that several sensor half elements carry the same sensor compounds 4, 5. Both methods lead to a built-in redundancy implying that multiple individual sensors are chemically and functional identical. By these means, the signal to noise ratio can be increased at the cost of the total integration density. Such a trade-off may become important for the measurements of rare analytes with small detectable total numbers which noticeably underlie a Poisson distribution. The built in parallel measurements and redundancy will increase the confidence. Of course, those ratios are considered for the whole measurement process from the sample preparation up to its measurement, but also in the design of the sensor array.

Dielectric macromolecules like DNA can be directed into the gap region 31 through non-uniform electric fields, a process which is called dielectrophoresis and which increases the local concentrations of the analyte 9 in the sensor array junctions 31 and accelerates the molecular recognition events.

Signal enhancements can be enhanced through post labeling with materials which show strong interaction with alternating electric fields like conjugated polymers, metallic nanoparticles or other dielectrics.

Experimental Results

Experimental Confirmation Part I:
Proof-of-Principle of Sensor Arrays with Sensor Half Elements This experiment concerns the result shown in FIG. 13. The employed sensor array 12 contains sensor half elements 1, 2 which are supported by two common carrier plates 61, 62. The junction areas 31 are defined as round spots which are placed on the first sensor half element 1. The second sensor half element 2 has not been structured and consists of a homogeneously functionalized surface. The focus of this demonstration is the specific analyte 9 amplification of a 400 nucleotide long template 9 between two surfaces. The experiment demonstrates the principle of the dual solid phase amplification reaction.

The First Sensor Half-Element:

One N-hydroxysuccinimide activated 75×25>1 mm glass slide from a commercial supplier, PolyAn, Germany, is the first carrier 71 and was used to immobilize amino-modified DNA oligonucleotides by contact spotting. The spotting solutions contained 20 μM of individual primers or 10 μM plus 10 μM of dual primer mixtures. Forward primer, reverse primer, the combination of both and a fluorescently modified guide dot oligonucleotides have been spotted to designated areas. The forward primer 4 is complementary to the 5'-site of the template 9 and the reverse primer 5 identical to the 3'-site of the template 9. The spotting produced a number of identical arrays with spot sizes of 120 μm diameter. The spotted DNA reacted for 12 hours at room temperature in a chamber of approximately 30% humidity which has been adjusted by saturated NaCl solution. Then, the surface has been immersed in blocking solution of 50 mM ethanolamine and 100 mM Tris at pH 9 for 15 minutes before rinsing it with water. A fluorescence scan, shown in FIG. 13, proved the quality of the array based on the amount of bound guide dot. The glass slide is the first sensor half element 1, one surface which carries a separate spots of forward and reverse primer sensor compounds 4. The mixed primers 4, 5 and guide dot oligonucleotides are for control purpose only.

The Second Sensor Half-Element:

For the second carrier 72 22×22×0.3 mm glass cover slides are used and were immersed in freshly prepared 3% 3-Methacryloxypropyltrimethoxysilane in 95% ethanol silanization solution. This process crafted a homogeneous reactive layer at the surface. After rinsing twice in ethanol the cover slide was baked for 15 minutes at 80° C. A mask has been made from a 94 μm thick adhesive plastic film consisting of a 3.5 mm frame and a square-shaped central void. Aminoreactive polymer has been produced by liquid-phase co-polymerization of mixed polyacrylamide, bis-acrylamide and glycidyl-methacrylate. For this purpose, 50 μl of polymerization solution was spread into the void area and immediately covered with a hydrophobically silanized glass plate. The polymerization reaction proceeded for two hours at room temperature before the cover slide has been transferred into 10 ml water. The mask was easily removed from the cover slide leaving just the covalently bound gel pad at the void area. For the functionalization 20 µl of a 0.5 µM amino-modified reverse primer solution have been spread across the gel surface which was subsequently incubation in a humidity chamber for two hours at room temperature. The binding reaction was stopped by immersing the cover slide in blocking solution for 15 minutes. Extensive rinsing with water removed all not bound reverse primers. The glass cover slide is the second sensor half element 2, one surface which carries the reverse primer sensor compound 5.

Assembly and PCR Cycling:

50 µl of a PCR mix which included a buffered system with 24 ng template DNA, bovine serum albumin, Trehalose, dNTP mix, Alexa Cy3 fluorescently labeled dCTP, Ficoll and Taq Hotstar Polymerase were applied to the first sensor half element 1. Ficoll is a water soluble polymer to self-seal a thin film fluidic reaction chamber at the contact with air. The second sensor half element 2 has been placed on top. The direct mechanical contact between gel pad and array has been enforced by gently squeezing out excess PCR mix. PCR cycling is started immediately afterwards and performed for 50 cycles of 95° C. for 30 sec, 62° C. for 30 sec and 70° C. for 2 min.

Screening of the Sensor Array:

Separation of the surfaces of the two sensor half elements 1, 2 is achieved by immersing the sensor array in a 2× saline-sodium citrate buffer and 0.01% sodium dodecyl sulfate washing solution for 10 minutes. The cover slide sensor half element 2 can be removed. Several washing steps with buffer in stepwise dilutions and finally water dilute any remaining PCR mix components and unbound reaction mix from the surface of the sensor half element 1. The glass slide 1 has been dried with pressurized air before scanning the surface with a Genepix 4000B fluorescence scanner from Axon. Fluorescence values were recorded through 532 nm laser light excitation coupled with a Cy3 optimized emission filter system. One representative sensor array section is shown in FIG. 13 as black and white scan. It contains two rows of 6 spots each of the forward primer 4, one row of the reverse primer 5, the mixed primer combination 4, 5 and the guide dots. The combination of the forward primer 4 from the first glass slide sensor half element 1 and the reverse primer 5 from the second sensor half element 2 yields the highest signals with more than 8500 counts. The background extension level is seen with around 500 counts at spots where the reverse primers 5 from both sensor half element surfaces 1, 2 faced each other in the second row. The mixed primers display a combination of interfacial amplification of an effective half concentrated forward primer 4 and reverse primer 5 combination analogue rows 1 and 5, and the contribution from the possible bridge amplification mechanism between the both primers 4, 5 at the sensor half element 1.

REFERENCES CITED

Patents Publications

Eggers M. D., Hogan M. E. (1996) Multi-site detection apparatus, U.S. Pat. No. 5,532,128, Houston Advanced Res Center.

Gao Z., Chen X. (2010) Electrical Sensor for ultrasensitive nucleic acid detection. WO 2010/104479 A1, Agency for Science, Technology and Research.

Maeda H. (2004) Sensor cell, bio-sensor, capacitance element manufacturing method, biological reaction detection method and genetic analytical method. US 20040110277, SEIKO EPSON CORP.

Lee B. C., Moon S. W. (2009) Biosensor having 3D metallic nanowire electrodes forming nanochannel, manufacturing method thereof, and bio disk system having same. EP 2088430A1, Korea Institute of Science and Technology.

Seitz A. (2007) Polynucleotide amplification, WO 2007062445 A1, Inventor.

Steinmüller-Nethl D. et al. (2009) Methode for identifying and quantifying organic and biochemical substances. WO 2009/003208 A1, ARC Austrian Research Centers.

Other Publications

Adessi C., Matton G., Ayala G., Turcatti G., Mermod J.-J., Mayer P., Kawashima E. (2000) Solid phase DNA amplification: characterisation of primer attachment and amplification mechanisms Nucl. Acids Res. 28 (20) e87

Carminati M., Ferrari G., Sampietro M. (2009) Attofarad resolution potentiostat for electrochemical measurements on nanoscale biomolecular interfacial systems. Rev. Sci. Instrum. 80(12), 124701

Hwang J. S., Kong K. J., Ahn D., Lee G. S., Ahn D. J., and Hwang S. W. (2002) Electrical transport through 60 base pairs of poly(dG)-poly(dC) DNA molecules. Appl. Phys. Lett. 81, 1134

Iqbal S. M., Balasundaram G., Subhasis Ghosh, Bergstrom D. E., Bashir R. (2005) Direct current electrical characterization of ds-DNA in nanogap junctions. Appl. Phys. Lett. 86(15):153901

Mercier J.-F., Slater G. W. (2003) Solid Phase DNA Amplification: A Brownian Dynamics Study of Crowding Effects. Biophysical Journal 89 (1) 32-42

Reed M. A., Zhou C., Muller C. J., Burgin T. P., Tour J. M. (1997) Conductance of a Molecular Junction. Science 278(5336):252-54

Reichert J., Ochs R., Beckmann D., Weber H. B., Löhneyssen H. v. (2002) Driving current through single organic molecules. Physical Review Letters 88:176804

Takashima S., Gabriel C., Sheppar R. J., Grant E. H. (1984) Dielectric behavior of DNA solution at radio and microwave frequencies (at 20 degrees C.). Biophys J. 46(1): 29-34

The invention claimed is:

1. A sensor array for identifying and/or quantifying a plurality of organic target compounds in a mixture of compounds, the sensor array comprising:
   at least two spatially separated, functionalized sensor half elements;
   each said sensor half element having one or more surface regions functionalized with one or more sensor compounds each;
   said sensor half elements being assembled in such a manner that respectively two or more sensor compounds from different sensor half elements are spaced and/or converge and/or contact each other in separate junction areas;
   said junction areas forming a plurality of single sensors for binding to specific kinds of the organic target compounds;
   said sensor half elements are aligned in a grid structure, with a plurality of row elements and a plurality of column elements;
   all said row elements being aligned on, or included in, or crafted of a first common carrier;

all said column elements being aligned on, or included in, or crafted of a second common carrier;
said first common carrier and/or said second common carrier being formed as a plate; and
wherein said surfaces of said sensor half elements are individually functionalized prior to an assembly of the sensor array.

2. The sensor array according to claim 1, wherein:
a first plurality of sensor compounds is formed or arranged in surface regions on said first common carrier;
a second plurality of sensor compounds is formed or arranged in surface regions on said second common carrier; and
each said junction area forms one single sensor with a predetermined combination of two or more sensor compounds disposed on two sensor half elements that are spaced from and/or converge and/or contact each other.

3. The sensor array according to claim 1, wherein:
said row elements are formed by a plurality of sensor half elements and said column elements are formed by a plurality of sensor half elements;
said row elements are aligned and spaced next to each other and said column elements are aligned and spaced next to each other;
each said row element intersects at least one said column element in at least one junction area; and
each said junction area forms an individual sensor.

4. The sensor array according to claim 1, wherein at least one or more of the following are true:
surface regions of said sensor half elements are longitudinally delineated and/or separated;
each surface region of said sensor half elements is functionalized with a different sensor compound;
each said sensor half element has a same number of delineated surface regions;
at least one or all said sensor half elements are made of carrier material or contain carrier material or support a carrier material layer, the carrier material or the carrier material layer being functionalized with one or more of said sensor compounds; and/or
said carrier materials or said carrier material layers of all said sensor half elements are identical.

5. The sensor array according to claim 1, wherein:
at least one of, or all of, said sensor half elements comprise a carrier; and
the respective said sensor compound is deposited as a layer on the respective said carrier.

6. The sensor array according to claim 5, wherein at least one or all said sensor half elements have a carrier made from a material selected from the group consisting of a filament, a string, a wire, a band, a bar, and a fiber.

7. The sensor array according to claim 1, wherein:
said sensor half elements are aligned in a grid structure, with a plurality of row elements and a plurality of column elements;
a number of functionalized surface regions on said row elements equals a number of said column elements,
each surface region of each said row element is allocated to and at least partially delimits or defines one said junction area; and/or
a number of functionalized surface regions on said column elements equals a number of row elements; and
each surface region of each said column element is allocated to and at least partially delimits or defines one said junction area.

8. The sensor array according to claim 1, wherein:
at least one of said sensor half elements carries a material layer that is functionalized with a sensor compound; and/or
said surface regions of at least one of said sensor half elements are functionalized with sensor compounds and are disjoint or discontiguous.

9. The sensor array according to claim 8, wherein:
all of said sensor half elements carry a material layer that is functionalized with a sensor compound; and/or
said surface regions of all of said sensor half elements are functionalized with sensor compounds.

10. The sensor array according to claim 1, wherein:
said sensor half elements comprise electrically or optically conducting carriers or waveguides, with said surface regions of said carriers or waveguides being functionalized with the respective sensor compounds; and/or
each said conducting carrier or waveguide is coated with an insulating layer; and/or
parts of the surface or exclusively only said surface regions of said junction areas are coated with an insulating layer; and/or
that the insulating layer contains, or is functionalized with, the respective sensor compound and/or
said insulating layer is covered with an additional layer which contains or is functionalized with the respective sensor compound.

11. The sensor array according to claim 10, wherein said electrically or optically conducting carriers or waveguides are made from metal, carbon fiber, conducting polymer, or glass fiber, and said additional layer is made from a polymer or a gel.

12. The sensor array according to claim 1, wherein:
said sensor half elements are aligned in a grid structure, with a plurality of row elements and a plurality of column elements;
said sensor half elements are straight and contact each other in the respective junction area; and/or
said sensor half elements are curved and contact each other in the respective junction area; and/or
said row elements are aligned in a first plane and said column elements are aligned in a second plane, and said row elements and said column elements are arranged in close proximity to or converge to or contact each other in said junction areas.

13. The sensor array according to claim 1, wherein:
said sensor half elements are aligned in a grid structure, with a plurality of row elements and a plurality of column elements;
all of said row elements are aligned on or included in or are crafted of one common carrier; and/or
all of said column elements are aligned on or included in or are crafted of a second common carrier.

14. The sensor array according to claim 1, wherein:
at least a portion of a circumference of a cross section of said sensor half elements is convex; and/or
a gap of said junction area between said sensor half elements is at least partially cuneiform and/or slit-shaped and/or said gap comprises a narrowing region; and/or
said sensor half elements contain a structured and/or wavelike and/or porous and/or rough surface; and/or
said sensor half elements are arranged on elevations or in cavities of said first common carrier and/or of said second common carrier.

15. The sensor array according to claim 1, wherein:
said sensor half elements are aligned in a grid structure, with a plurality of row sensor elements and a plurality of column sensor elements;
within said junction areas, the molecules of the sensor compound of said row sensor elements and the molecules of the sensor compound of said column sensor elements are spaced at most in a manner that the organic compounds under investigation or one of its related copies are able to bind to the respective sensor compound arranged on said row sensor elements with a first binding site and to the respective sensor compound arranged on said column sensor elements with a second binding site; and/or
the respective sensor compounds of said sensor half elements contain oligonucleotides, binding to binding sites of the target compounds or organic polymers or DNA or RNA molecules; and/or
the respective sensor compounds of said row sensor elements bind to start sites of organic polymers or DNA or RNA molecules and the respective sensor compounds of said column sensor elements bind to end sites of organic polymers or DNA or RNA molecules.

\* \* \* \* \*